United States Patent [19]

Carroll et al.

[11] Patent Number: 4,846,996
[45] Date of Patent: Jul. 11, 1989

[54] LIQUID, NON-CRYSTALLIZING TWO MOLE DIPHENOL ALKOXYLATE MIXTURES

[75] Inventors: Clifford C. Carroll, Spartanburg; John W. Miley, Campobello; Richard A. Van Dahm, Spartanburg, all of S.C.

[73] Assignee: Milliken Research Corporation, Spartanburg, S.C.

[21] Appl. No.: 154,697

[22] Filed: Feb. 11, 1988

[51] Int. Cl.$^4$ .............................................. C08G 63/68
[52] U.S. Cl. ........................... 252/182.16; 252/182.17; 252/182.25
[58] Field of Search ...................... 252/182.16, 182.17, 252/182.25, 182.27

[56] References Cited

U.S. PATENT DOCUMENTS

| | | | |
|---|---|---|---|
| 3,497,465 | 2/1970 | Kujawa et al. | 252/182.25 |
| 3,639,294 | 2/1972 | Burns et al. | 252/182.16 |
| 3,639,295 | 2/1972 | Burns et al. | 252/182.16 |
| 3,943,077 | 3/1976 | Bell et al. | 252/182.25 |
| 4,046,742 | 9/1977 | Eimers et al. | 252/182.16 |
| 4,170,587 | 10/1979 | Schmidt et al. | 252/182.16 |
| 4,251,385 | 2/1981 | Sigan et al. | 252/182.16 |

OTHER PUBLICATIONS

Diamond Shamrock Publication (1981) Product Bulletin on Colok® 265.
Diamond Shamrock brochure entitled "TIPS".
Akzo Chemie America Technical Bulletin dated 1985, p. 19.

*Primary Examiner*—Edward A. Miller
*Attorney, Agent, or Firm*—Terry T. Moyer; H. William Petry

[57] ABSTRACT

A mixture of diphenols is provided of the general formula:

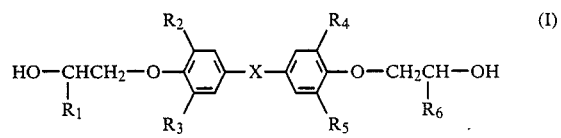

wherein the mixture comprises three components as follows;

(a) from about 2% to about 35% by weight of compound A corresponding to formula (I) wherein $R_1$ and $R_6$ are H; $R_2$, $R_3$, $R_4$ and $R_5$ are selected from H and Br; and —X— is selected from $CH_3$—C—$CH_3$, —S—, or —O—;

(b) from about 15% to about 50% by weight of compound B corresponding to formula (I) wherein $R_1$ is H; $R_6$ is $CH_3$; $R_2$, $R_3$, $R_4$, $R_5$ are selected from H or Br; and —X— is selected from $CH_3$—C—$CH_3$, —S—, or —O—; and (c) from about 15% to about 80% by weight of compound C corresponding to formula (I) wherein $R_1$ and $R_6$ are $CH_3$; $R_2$, $R_3$, $R_4$ and $R_5$ are selected from H or Br; and —X— is selected from $CH_3$—C—$CH_3$, —S—, or —O—.

5 Claims, No Drawings

LIQUID, NON-CRYSTALLIZING TWO MOLE DIPHENOL ALKOXYLATE MIXTURES

The present invention relates to a two mole, diphenol alkoxylate mixture. More particularly, the present invention relates to a liquid, non-crystallizing, two mole diphenol alkoxylate mixture prepared by the reaction of a mixture two different alkylene oxides with a diphenol in the presence of an alkaline catalyst.

Two mole alkoxylates of diphenols have found wide use as specialty monomers in numerous thermoplastic and thermoset resin systems. They are used as monomers in the preparation of resistant polyester resins and alkyd resins and also as chain extenders or curatives for polyurethanes. Incorporation of these monomers into these resin systems is claimed to impart enhancements in chemical resistance, flexibility, adhesion, and processability to the resin system (Akzo Chemie America, Chicago, Ill., Technical Bulletin (1985), Diamond Shamrock Corp., Morristown, N.J., Product Bulletin (1981). Two of the most commonly used two mole diphenol alkoxylates are 2,2'-(1-methylethylidene)bis(4,1-phenyleneoxy)bisethanol and 1,1'-(1-methylethylidene)bis(4,1-phenyleneoxy)bis-2-propanol, both of which are commercially available from several suppliers.

One of the disadvantages to the use of these materials is the fact that they are both solids at room temperature. The 2,2'-(1-methylethylidene)bis(4,1-phenyleneoxy)-bisethanol melts at a temperature of around 110° C. and the 1,1'-(1-methylethylidene)bis(4,1-phenyleneoxy)bis-2-propanol melts at a temperature of around 65° C. This property makes both of these materials considerably more difficult to handle than ordinary liquid diols and special equipment and procedures are needed to handle these materials. Several means are employed to ease the handling of these materials. One means is to flake or granulate the materials during their manufacture. These measures add extra expense to the manufacturing process and they also lead to a decrease in the amount of material which can be placed in a shipping container, again leading to extra expense. Finally, provisions must be made to handle any dusting associated with these materials during their use. A second means of handling these materials is to maintain them above their melting points from manufacture to subsequent use or to ship them as cast solids and remelt them prior to use, again adding expense to the products in terms of energy and heated storage and shipping equipment. Prolonged exposure to elevated temperatures may also lead to possible degradation of the products and it poses potential dangers in handling the products at high temperatures.

Solid handling problems may of course be avoided if a liquid product is produced. This may be accomplished by increasing the oxyalkylene content of the alkoxylated diphenol. Increasing the oxyalkylene content can, however, lead to increased water sensitivity and to a degradation in the thermomechanical properties of the resin system in which the alkoxylated diphenol is used (Parklyn, B., Lamb, F., Clifton, B. V., Polyesters, Vol. 2, American Elsevier, 32 (1967). Problems associated with increasing the oxyalkylene content may be avoided by preparing a liquid, eutectic mixture of two different dialkoxylated diphenols. An example of such a mixture would be a 50/50 blend of 2,2'-(1-methylethylidene)bis(4,1-phenyleneoxy)bisethanol and 1,1'-(1-methylethylidene)bis(4,1-phenyleneoxy)bis-2-propanol. While this mixture is initially a clear viscous liquid at room temperature, however, after a period of time it begins to partially crystallize, which is undesirable in a product of this type.

The dialkoxylated diphenols mixture of this invention may overcome these objections. It is a liquid at room temperature and may not crystallize even when stored for long periods of time at subambient temperatures. The mixtures may, furthermore, be manufactured without the use of any flaking or granulating equipment and may be handled as a liquid during subsequent use. It does not require the use of any special shipping or storage procedures to prevent solidification and it does not require remelting prior to use. Potential degradation due to prolonged exposure to elevated temperatures may be avoided.

According to the present invention a mixture of diphenols is provided of the general formula:

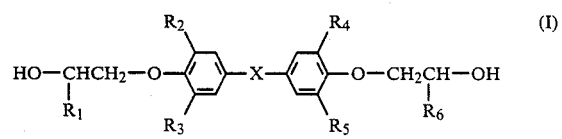

wherein the mixture comprises three components as follows:

(a) from about 2% to about 35% by weight of compound A corresponding to formula (I) wherein $R_1$ and $R_6$ are H; $R_2$, $R_3$, $R_4$ and $R_5$ are selected from H and Br; and —X— is selected from

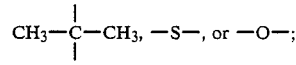

(b) from about 15% to about 50% by weight of compound B corresponding to formula (I) wherein $R_1$ is H; $R_6$ is $CH_3$; $R_2$, $R_3$, $R_4$, $R_5$ are selected from H or Br; and —X— is selected from

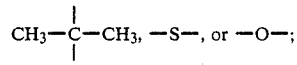

and (c) from about 15% to about 80% by weight of compound C corresponding to formula (I) wherein $R_1$ and $R_6$ are $CH_3$; $R_2$, $R_3$, $R_4$ and $R_5$ are selected from H or Br; and —X— is selected from

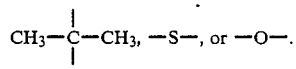

With regard to the mixture described above the preferred range for the amount of compound A is from about 15% to about 25% by weight. The preferred amount of compound B present in the mixture is from about 45% to about 50% by weight and the preferred amount of compound C in the mixture is from about 25% to about 40% by weight.

Mixtures having distributions outside of the ranges set forth above for compounds A, B and C are solids or have a tendency to crystallize at subambient temperatures. The compositions of the present invention may be prepared through the reaction of a mixture of alkylene oxides with a diphenol in the presence of an alkaline catalyst. The alkylene oxides preferred are ethylene oxide and propylene oxide. Examples of diphenols which may be useful are 4,4'-(1-methylethylidene)bisphenol, 4,4'-methylene bisphenol, 4,4'-thiobisphenol, 4,4'-(1-methylethylidene)bis(3,4-dibromophenol) and the like. The preferred diphenol is 4,4'-(1-methylethylidene)bisphenol. The preferred alkaline catalyst for the process is of the tertiary aliphatic amine type such as triethylamine, tri-n-propylamine, N,N-dimethylcyclohexylamine and other such catalysts. The preferred catalyst is tri-n-propylamine.

More specifically, the mixtures of the invention may be prepared by contacting a diphenol with a two molar mixture of ethylene and propylene oxide in the presence of from about 0.01% to about 2% of an alkaline catalyst at temperatures of from about 100° C. to about 200° C. until all the alkylene oxide has reacted. The reaction may be carried out in the presence of suitable solvent such as toluene or methylisobutylketone if necessary. Alternatively, the diphenol may be allowed to react with one molar equivalent of ethylene oxide followed by one molar equivalent of propylene oxide or visa versa. In either case the results are essentially the same.

The liquid dialkoxylated diphenol mixtures of the present invention are useful in the preparation of unsaturated polyester resins. Thus, when an approximately equal molar amount of one of the mixtures is esterified with an unsaturated dicarboxylated acid or anhydride such as fumaric acid or maleic anhydride in the presence of an esterification catalyst, an unsaturated polyester resin is obtained. The resin is copolymerizable with ethenically unsaturated materials such as styrene in the presence of an organic peroxide catalyst and yields a hard, tough, crosslinked resin.

The liquid dialkoxylated diphenol mixtures are also useful as chain extenders in polyurethane elastomers systems. Thus, when a urethane prepolymer such as one resulting from the reaction of a polycaprolactone with an approximately one molar equivalent of toluene diisocyanate is combined with an equal molar amount of one of the dialkoxylated diphenol mixtures in the presence of a suitable catalyst and the resulting mixture cured at 140° C. a elastomeric polyurethane is obtained.

The following examples are illustrative of the preparation and use of this invention, but are not to be construed as limiting the scope of the invention which is defined in the claims appended hereto. Unless otherwise indicated all parts and percentages are by weight.

EXAMPLE 1

Nine hundred and twelve grams of 4,4'-(1-methylethylidene)bisphenol, 200 grams of methylisobutylketone and 4.5 grams of tri-n-propylamine were added to an autoclave. The autoclave was then sealed, purged with nitrogen, and then pressurized to 5 PSIG with nitrogen. The contents of the autoclave were then heated to 145°-150° C. and maintained at that temperature while 360 grams of ethylene oxide was added over a 5 hour time period. During the ethylene oxide addition the pressure was maintained below 70 PSIG. After the ethylene oxide addition was complete the reaction mixture was post-cooked for 1 hour at 145°-150° C. The reaction mixture was then cooled to 120° C. and vacuum stripped to remove solvent and excess ethylene oxide. The resulting 2,2'-(1-methylethylidene)bis(4,1-phenyleneoxy)bisethanol had a melting point of 108° C., a hydroxyl number of 353.5 and a purity of 98.2 as determined by gas chromatography.

EXAMPLE 2

Following the procedure of Example 1, 470 grams of propylene oxide was added to a mixture of 912 grams of 4,4'-(1-methylethylidene)bisphenol and 4.5 grams of tri-n-propylamine in 200 grams of methylisobutylketone at 145°-150° C. over a period of 5 hours. The reaction mixture was stripped at 110° C. to remove solvent and residual propylene oxide. The resulting 1,1'-(1-methylethyl-idene)bis(4,1-phenyleneoxy)bis-2-propanol has a melting point of 63° C., a hydroxyl number of 324 and a purity of 97.4 as determined by gas chromatography.

EXAMPLE 3

Comparative Example

Mixtures of 2,2'-(1-methylethylidene)bis(4,1-phenyleneoxy)bisethanol, I, and 1,1'-(1-methylethylene)bis(4,1-phenyleneoxy)bis-2-propanol, II, were prepared by mixing the two together while in the molten state. The mixtures prepared are shown in Table I.

TABLE I

| | Mixture | | | | | | | | |
|---|---|---|---|---|---|---|---|---|---|
| | 1 | 2 | 3 | 4 | 5 | 6 | 7 | 8 | 9 |
| Weight % I | 10 | 20 | 30 | 40 | 50 | 60 | 70 | 80 | 90 |
| Weight % II | 90 | 80 | 70 | 60 | 50 | 40 | 30 | 20 | 10 |

The mixtures were allowed to cool to room temperature and observed over a period of several days. After setting for 5 days all of the mixtures had begun to crystallize.

EXAMPLES 4-10

A series of reactions were carried out wherein the ratio of propylene oxide (PO) to ethylene oxide (EO) was varied in the alkylene oxide mixture. The reaction conditions and procedures used were the same as those used in Example 2 with the various mixtures of ethylene and propylene oxide substituted for the propylene oxide charge. Table 2 lists the alkylene oxide charges. In all cases 912 grams of 4,4'-(1-methylethylidene)bisphenol was used as the diphenol. Upon completion, the reaction products were examined by means of High Pressure Liquid Chromatography in conjunction with Mass Spectroscopy to determine the identity and the amount of the individual components present in the product. This examination showed the product to be a mixture of three major components. These were identified as 1,1'-(1-methylethylidene)-bis(4,1-phenyleneoxy)bisethanol (Component A), 2,2'-(1-methylethylidene)bis(4,1-phenyleneoxy)bis-2-propanol (Component B), and 1-(2-hydroxyethyl)-1'-(2-hydroxypropyl)-(4,4'-(1-methylethylidene)bisphenol) (Component C). The amount of each of these products present is listed in Table 2.

TABLE 2

| Example Number | EO Charge | PO Charge | EO/PO Ratio | Hydroxyl Number | Component, Wt. % | | |
|---|---|---|---|---|---|---|---|
| | | | | | A | B | C |
| 4 | 35 | 418 | 10/90 | 328 | 2.1 | 79.4 | 16.7 |
| 5 | 70 | 371 | 20/80 | 330 | 3.7 | 62.8 | 31.2 |
| 6 | 141 | 279 | 40/60 | 338 | 15.2 | 36.9 | 45.8 |

TABLE 2-continued

| Example Number | EO Charge | PO Charge | EO/PO Ratio | Hydroxyl Number | Component, Wt. % | | |
|---|---|---|---|---|---|---|---|
| | | | | | A | B | C |
| 7 | 176 | 232 | 50/50 | 339 | 24.2 | 25.4 | 49.0 |
| 8 | 194 | 209 | 55/45 | 341 | 30.9 | 19.7 | 48.7 |
| 9 | 211 | 186 | 60/40 | 344 | 39.5 | 14.2 | 46.8 |
| 10 | 282 | 93 | 80/20 | 348 | 60.3 | 4.6 | 33.5 |

Examples 4–8 remained liquid upon cooling to room temperature while Examples 9 and 10 solidified.

EXAMPLE 11

Samples of the products of Examples 4–10 were placed in a freezer at −18° C. and checked daily for signs of crystallization. After a period of one month no crystallization had occurred.

EXAMPLE 12

Eight hundred grams of 4,4′-methylenebisphenol were allowed to react with a mixture of 176 grams of ethylene oxide and 232 grams of propylene oxide in the presence of 4.5 grams of tri-n-propyl amine catalyst and 200 grams of methylisobutylketone solvent. The reaction conditions and procedures used were identical to those used in Example 7 above. After the reaction was complete the product was analyzed by means of High Pressure Liquid Chromatography and it was determined to be a mixture of 2,2′-(methylenebis-4,1-phenyleneoxy)bisethanol, 1,1′-(methylenebis-4,1-phenyleneoxy)bis-2-propanol, and 1-(2-hydroxyethyl)-1′-(2-hydroxypropyl)-4,4′-methylenebisphenol. The product had a hydroxyl number of 371 and was liquid at room temperature. Storage at −18° C. for 1 month did not result in any crystallization.

EXAMPLE 13

Using the procedure detailed in Example 7, 872 grams of 4,4′-thiobisphenol was allowed to react with a mixture of 176 grams of ethylene oxide and 232 grams of propylene oxide in the presence of 4.5 grams of tri-n-propylamine catalyst and 200 grams methylisobutylketone solvent. The reaction yielded a liquid mixture of 2,2′-(thiobis-4,1-phenyleneoxy)bisethanol, 1,1′-(thiobis-4,1-phenyleneoxy)bis-2-propanol, and 1-(2-hydroxyethyl)-1′-(2-hydroxypropyl)-4,4′-thiobisphenol. The product had a hydroxyl number of 349 and exhibited no signs of crystallization when stored at room temperature.

EXAMPLE 14

Using the procedure detailed in Example 7, 816 grams of 4,4′-(1-methylethylidene)bis(2,6-dibromophenol) was allowed to react with a mixture of 66 grams of ethylene oxide and 87 grams of propylene oxide in the presence of 2.0 grams of tri-n-propyl-amine and 200 grams of methylisobutylketone solvent. The reaction afforded a liquid mixture of 2,2′-(1-methylethylidene)-bis[4,1-(2,6-dibromophenyleneoxy)]bis-2-propanol, and 1-(2-hydroxyethyl)-1′-(2-hydroxypropyl)-4,4′-(2,6-dibromophenol) having a hydroxyl number of 175. The product was liquid at room temperature and did not crystallize after 3 month's storage.

EXAMPLE 15

Three hundred five grams of the product of Example 7 was heated with 91 grams of maleic anhydride, 0.1 grams of hydroquinone, and 1.2 grams of p-toluenesulfonic acid at 190° C. for 5 hours under nitrogen. The resulting product was then vacuum stripped for 15 minutes at 190° C. to afford a solid, unsaturated polyester resin having an acid number of 2. Fifty grams of the solid resin was then dissolved in 50 grams of styrene and the resulting mixture cured to a hard crosslinked, resin casting using catalytic amounts of benzoyl peroxide and cobalt naphthanate. The cured resin had a Durameter hardness of 87.5.

What is claimed is:

1. A liquid non-crystallizing two mole diphenol alkoxylate mixture of the general formula:

$$HO-CHCH_2-O-\overset{R_2\quad\quad R_4}{\underset{R_3\quad\quad R_5}{\text{─}\phantom{X}\text{─}}}-X-\overset{}{\underset{}{\text{─}\phantom{X}\text{─}}}-O-CH_2CH-OH \quad (I)$$
$$\phantom{HO-CH}R_1 \phantom{CH_2-O-XXXXXXXXXXXXXXXX} R_6$$

wherein the mixture comprises three components as follows:

(a) from about 2% to about 35% by weight of compound A corresponding to formula (I) wherein $R_1$ and $R_6$ are H; $R_2$, $R_3$, $R_4$ and $R_5$ are selected from H and Br; and —X— is selected from $$CH_3-\underset{|}{\overset{|}{C}}-CH_3, -S-, \text{ or } -O-;$$

(b) from about 15% to about 50% by weight of compound B corresponding to formula (I) wherein $R_1$ is H; $R_6$ is $CH_3$; $R_2$, $R_3$, $R_4$, $R_5$ are selected from H or Br; and —X— is selected from $$CH_3-\underset{|}{\overset{|}{C}}-CH_3, -S-, \text{ or } -O-;$$

and (c) from about 15% to about 80% by weight of compound C corresponding to formula (I) wherein $R_1$ and $R_6$ are $CH_3$; $R_2$, $R_3$, $R_4$ and $R_5$ are selected from H or Br; and —X— is selected from $$CH_3-\underset{|}{\overset{|}{C}}-CH_3, -S-, \text{ or } -O-.$$

2. The mixture of claim 1 wherein —X— is $$CH_3-\underset{|}{\overset{|}{C}}-CH_3.$$

3. The mixture of claim 1 wherein —X— is —S—.
4. The mixture of claim 1 wherein —X— is —O—.
5. The mixture of claim 1 wherein compound A is present in an amount of from about 15% to about 25% by weight, compound B is present in an amount of from about 45% to about 50% by weight and compound C is present in an amount of from about 25% to about 40% by weight.

* * * * *